United States Patent
Donnelly

(10) Patent No.: US 11,744,247 B2
(45) Date of Patent: *Sep. 5, 2023

(54) DERMAL COMPOSITIONS

(71) Applicant: Neogen Corporation, Lansing, MI (US)

(72) Inventor: Martin Donnelly, Nottingham (GB)

(73) Assignee: NEOGEN CORPORATION, Lansing, MI (US)

( * ) Notice: Subject to any disclaimer, the term of this patent is extended or adjusted under 35 U.S.C. 154(b) by 354 days.

This patent is subject to a terminal disclaimer.

(21) Appl. No.: 16/855,907

(22) Filed: Apr. 22, 2020

(65) Prior Publication Data

US 2020/0245622 A1    Aug. 6, 2020

Related U.S. Application Data

(63) Continuation of application No. 14/809,030, filed on Jul. 24, 2015, now Pat. No. 10,721,930.

(60) Provisional application No. 62/096,361, filed on Dec. 23, 2014.

(51) Int. Cl.

| | |
|---|---|
| *A01N 43/00* | (2006.01) |
| *A01N 43/46* | (2006.01) |
| *A61K 31/55* | (2006.01) |
| *A01N 43/50* | (2006.01) |
| *A01N 37/08* | (2006.01) |
| *A61K 9/00* | (2006.01) |
| *A61K 31/4439* | (2006.01) |
| *A61K 31/215* | (2006.01) |
| *A61K 9/08* | (2006.01) |
| *A61K 47/20* | (2006.01) |
| *A61K 31/4402* | (2006.01) |
| *A61K 47/22* | (2006.01) |

(52) U.S. Cl.
CPC ............. *A01N 43/50* (2013.01); *A01N 37/08* (2013.01); *A61K 9/0017* (2013.01); *A61K 9/08* (2013.01); *A61K 31/215* (2013.01); *A61K 31/4402* (2013.01); *A61K 31/4439* (2013.01); *A61K 47/20* (2013.01); *A61K 47/22* (2013.01)

(58) Field of Classification Search
None
See application file for complete search history.

(56) References Cited

U.S. PATENT DOCUMENTS

| | | |
|---|---|---|
| 7,728,011 B2 | 6/2010 | Sirinyan et al. |
| 2004/0037869 A1 | 2/2004 | Cleverly et al. |
| 2014/0148339 A1* | 5/2014 | Smejkal ............... A61P 33/14 540/554 |

FOREIGN PATENT DOCUMENTS

| | | |
|---|---|---|
| DE | 10117676 A1 | 10/2002 |
| EP | 1609362 A2 | 12/2005 |
| EP | 2266400 A1 | 12/2010 |
| WO | WO2008098168 A2 | 8/2008 |
| WO | WO-2014131786 A1 * | 9/2014 ............. A01N 51/00 |
| WO | WO2014131786 A1 | 9/2014 |
| WO | WO2014152980 A1 | 9/2014 |

OTHER PUBLICATIONS

Extended European Search Report for European Patent Application No. 15201705.9, dated Apr. 22, 2016 (7 pages).

* cited by examiner

*Primary Examiner* — Layla Soroush

(74) *Attorney, Agent, or Firm* — Honigman LLP; Douglas H. Siegel

(57) ABSTRACT

Disclosed herein are veterinary compositions including imidacloprid or an analogue thereof; a pyrethroid; a solvent selected from the group consisting of N-methyl pyrrolidone, N-ethyl pyrrolidone and mixtures thereof; and dimethyl sulfoxide. The veterinary compositions of the invention are useful in methods of controlling parasites on or within warm-blooded domesticated animals.

9 Claims, No Drawings

DERMAL COMPOSITIONS

The present invention relates to composition for treating parasites, in particular ticks and fleas, on an animal, in particular a dog.

Advantix® is a commercially available product which is marketed as being effective in treating ticks, flies and mosquitoes on a dog. It comprises both imidacloprid and permethrin as active ingredients and its formulation is described in U.S. Pat. No. 7,728,011. Advantix® is typically administered as a spot-on composition and the characteristics of the composition are such that it then spreads across the skin of the animal. In order to achieve this, while the action of the composition is not systemic, it is important that the composition penetrates through to the lower dermal layers.

While Advantix® has been demonstrated to be effective in the long term (i.e. over a period of 3 to 4 weeks) control of parasites on animals, in particular dogs, it suffers from the problem that the primary solvent with which it is formulated, N-methyl pyrrolidone (NMP), is a high risk solvent. More specifically, following the recent re-examination by the 31st Committee on the Adaptation to Technical Progress (31st ATP), of the EU directives for the elimination of technical barriers to trade with dangerous substances and preparations and, in accordance with EU directive 2009/2/EC dated 15 Jan. 2009, NMP is now classified as toxic (T classification) and reprotoxic of category 2 in the Risk-Phrasal R61. This means that it is considered to be teratogenic and so presents a handling risk during formulation. Similarly, it has been categorised as a class 2 solvent by the FDA.

The safety problem associated with NMP is well-documented and there has been a drive to identify an alternative safer solvent (see, for example, EP 2266400). In this regard, there have been various suggestions regarding an appropriate substitute but, because NMP is so effective at dissolving polar materials and their salts, it has proven difficult to identify an equivalent alternative. This is particularly a challenge in the formulation of a veterinary composition, where an alternative solvent needs to be identified without having any negative impact on the efficacy of the composition. This situation is further complicated where the composition includes more than one active ingredient.

SUMMARY OF INVENTION

Against this background, it is clear that there is a need for a veterinary composition which is as effective as commercially available products, such as Advantix®, but which does not suffer from the safety problems associated with using NMP as the sole primary solvent. With this in mind, the present inventor has investigated the use of alternative solvents.

However, despite indications to the contrary in various references, the applicant has surprisingly found that it is not possible to simply substitute a solvent indicated to be an alternative to NMP for NMP and still obtain a composition which is suitable for veterinary uses, even where the solvent has been specifically described as an alternative to NMP for formulating imidacloprid. An example of such as solvent is Armid® FMPC which is specifically marketed as an alternative to NMP for this very purpose (see http://www.sc.akzonobel.com/en/agriculture/Pages/news-armid-FMP-C.aspx). Without wishing to be bound by theory, it is believed that this is because the compositions with which the present invention is concerned comprise a combination of active ingredients, only one of which is imidacloprid and it is the presence of these further active ingredients which complicates the situation.

The present inventor has identified compositions which comprise both imidicaloprid and permethrin which can be formulated with less NMP than commercially available compositions and which surprisingly exhibit improved long term storage stability under low temperature conditions.

Accordingly, the present invention provides a veterinary composition which comprises imidacloprid or an analogue thereof, permethrin and dimethyl sulfoxide (DMSO). More specifically, the present invention provides a veterinary composition comprising;

0.1 to 20% by weight of imidacloprid or an analogue thereof; and 0.1 to 75% by weight of a pyrethroid;

wherein the balance of the composition by weight comprises a first solvent selected from the group consisting of N-methyl pyrrolidone, N-ethyl pyrrolidone and mixtures thereof and a second solvent which is dimethyl sulfoxide (DMSO) and wherein the composition optionally further comprises:

0 to 5% by weight of water;

0 to 0.5% by weight of an antioxidant;

0 to 2% by weight of at least one organic acid;

0 to 2% by weight of pyriproxifen;

0 to 40% by weight of further veterinary acceptable endoparasitic and exoparasitic agents; and 0 to 40% by weight of further veterinary acceptable excipients.

In another aspect, the present invention provides a veterinary composition comprising;

0.1 to 20% by weight of imidacloprid or an analogue thereof; and 0.1 to 75% by weight of a pyrethroid;

wherein the balance of the composition by weight comprises a first solvent selected from the group consisting of N-methyl pyrrolidone, N-ethyl pyrrolidone and mixtures thereof and a second solvent which is dimethyl sulfoxide (DMSO) and wherein the composition optionally further comprises:

0 to 5% by weight of water;

0 to 0.5% by weight of an antioxidant;

0 to 2% by weight of at least one organic acid;

0 to 2% by weight of pyriproxifen;

0 to 40% by weight of further veterinary acceptable endoparasitic and exoparasitic agents; and 0 to 40% by weight of further veterinary acceptable excipients, wherein the composition comprises less than 20% by weight of DMSO.

In some embodiments, the veterinary composition comprises less than 27.5% by weight of the first solvent. In certain embodiments, the veterinary composition comprises greater than 20% by weight of the first solvent.

In another aspect, the present invention provides a veterinary composition comprising;

0.1 to 20% by weight of imidacloprid or an analogue thereof; and 0.1 to 75% by weight of a pyrethroid;

wherein the balance of the composition by weight comprises a first solvent selected from the group consisting of N-methyl pyrrolidone, N-ethyl pyrrolidone and mixtures thereof and a second solvent which is dimethyl sulfoxide (DMSO) and wherein the composition optionally further comprises:

0 to 5% by weight of water;
0 to 0.5% by weight of an antioxidant;
0 to 2% by weight of at least one organic acid;
0 to 2% by weight of pyriproxifen;
0 to 40% by weight of further veterinary acceptable endoparasitic and exoparasitic agents; and
0 to 40% by weight of further veterinary acceptable excipients,
wherein the composition comprises greater than 20% by weight of the first solvent.

In one embodiment, the composition comprises less than 20% by weight of DMSO. In some embodiments, the composition comprises less than 27.5% by weight of the first solvent.

In another aspect, the invention provides a veterinary composition comprising:
0.1 to 20% by weight of imidacloprid or an analogue thereof;
0.1 to 75% by weight of a pyrethroid;
2.5 to 25% by weight of a solvent selected from the group consisting of N-methyl pyrrolidone, N-ethyl pyrrolidone and mixtures thereof;
2.5 to 97.3% by weight of dimethyl sulfoxide (DMSO);
0 to 5% by weight of water;
0 to 0.5% by weight of an antioxidant; and
0 to 2% by weight of at least one organic acid.

In some embodiments, the composition comprises less than 20% by weight of DMSO.

In a further aspect, the invention provides a veterinary composition comprising:
0.1 to 20% by weight of imidacloprid or an analogue thereof;
0.1 to 75% by weight of a pyrethroid;
greater than 20% and up to 25% by weight of a solvent selected from the group consisting of N-methyl pyrrolidone, N-ethyl pyrrolidone and mixtures thereof;
2.5 to 97.3% by weight of dimethyl sulfoxide (DMSO);
0 to 5% by weight of water;
0 to 0.5% by weight of an antioxidant; and
0 to 2% by weight of at least one organic acid.

In another aspect, the invention provides a veterinary composition comprising:
0.1 to 20% by weight of imidacloprid or an analogue thereof;
0.1 to 75% by weight of a pyrethroid;
greater than 20% and up to 25% by weight of a solvent selected from the group consisting of N-methyl pyrrolidone, N-ethyl pyrrolidone and mixtures thereof;
at least 2.5% and 20% by weight of dimethyl sulfoxide (DMSO);
0 to 5% by weight of water;
0 to 0.5% by weight of an antioxidant; and
0 to 2% by weight of at least one organic acid.

In yet another aspect, the invention provides a veterinary composition comprising:
0.1 to 20% by weight of imidacloprid;
0.1 to 75% by weight of a pyrethroid;
greater than 20% and up to 25% by weight of a first solvent selected from the group consisting of N-methyl pyrrolidone, N-ethyl pyrrolidone and mixtures thereof; and at least 2.5% and less than 20% by weight of a second solvent which is dimethyl sulfoxide (DMSO).

In some embodiments of any of the preceding aspects, the pyrethroid is permethrin. In certain such embodiments, the veterinary composition may comprise permethrin in an amount in the range from 25 to 75% by weight. In particular embodiments, the composition comprises 35 to 67.5% by weight of permethrin. In some embodiments, the composition comprises 2.5 to 12.5% by weight of imidacloprid or an analogue thereof.

In some embodiments of any of the preceding aspects, the first solvent is N-methyl pyrrolidone.

In some embodiments of any of the preceding aspects, the veterinary composition comprises greater than 10% by weight of DMSO (e.g., between 10% and 20% DMSO). In certain embodiments, the composition comprises greater than 15% by weight of DMSO (e.g., between 15% and 20% DMSO). In particular embodiments, the composition comprises greater than 17% by weight of DMSO (e.g., between 17% and 20% DMSO).

In some embodiments of any of the preceding aspects, the veterinary composition further comprises an antioxidant in an amount in the range from about 0.05% to about 0.25% by weight. In some embodiments of any of the preceding aspects, the veterinary composition further comprises at least one organic acid in an amount in the range from about 0.05% to about 1% by weight. In some embodiments of any of the preceding aspects, the veterinary composition further comprises pyriproxifen in an amount in the range from about 0% to about 2% by weight.

Veterinary compositions according to any of the preceding aspects can be used for dermal application. In some embodiments, the veterinary compositions are pour-on or spot-on formulations.

In certain embodiments of any of the preceding aspects, a veterinary composition is designed for use in controlling parasites on or within a warm-blooded domesticated animal. In some such embodiments, parasites are selected from the group consisting of ectoparasites, endoparasites, or both. In particular embodiments, parasites are selected from one or more of the groups consisting of fleas, ticks, mites, lice, intestinal worms, heartworms, and other internal worms. Most typically, the parasites are ectoparasites. In some embodiments, the animal is a small domesticated animal, such as a dog. In certain embodiments, a composition is applied dermally to the animal, and may be formulated as a pour-on or spot-on formulation.

The invention also features a method of controlling a parasite on or within a warm-blooded domesticated animal. The method involves the step of applying a veterinary composition of any of the preceding aspects to the skin of an animal to be treated.

In some embodiments of the method, parasites are selected from the group consisting of ectoparasites, endoparasites, or both. In particular embodiments, parasites are selected from one or more of the groups consisting of fleas, ticks, mites, lice, intestinal worms, heartworms, and other internal worms. In some embodiments, the animal is a dog.

Ranges provided herein are inclusive unless otherwise specified. For example, a composition comprising "0 to 5% by weight of water" may comprise 0% by weight of water or 5% by weight of water. Ranges provided using the term "between" are not inclusive. For example, a composition comprising "between 2.5% and 20% by weight of DMSO" may not comprise 2.5% by weight of DMSO or 20% by weight of DMSO. Such a composition could alternatively be described as comprising "greater than 2.5% and less than 20% by weight of DMSO." Ranges provided using the term "at least" and "up to" are inclusive. For example, a composition comprising "at least 2.5% and up to 20% by weight of DMSO" may comprise 2.5% by weight of DMSO or 20% by weight of DMSO.

DETAILED DESCRIPTION

The present invention features veterinary compositions and methods of using the same. Veterinary compositions of the invention include imidacloprid or an analogue thereof; a pyrethroid such as permethrin; a first solvent selected from the group consisting of N-methyl pyrrolidone, N-ethyl pyrrolidone and mixtures thereof; and a second solvent which is dimethyl sulfoxide (DMSO).

Advantageously, the present inventors have found that the veterinary compositions of the present invention provide equivalent efficacy to commercially available products such as Advantix® while not suffering from safety problems. In addition, the compositions have surprisingly been found to offer storage stability advantages over commercially available products. More specifically, no crystallisation is observed even after prolonged storage at low temperature conditions which is particularly relevant because such temperature conditions are likely to be encountered as a consequence of distribution across various climate zones.

The compositions of the present invention comprise imidacloprid or an analogue thereof. Imidacloprid (N-{1-[(6-Chloro-3-pyridyl)methyl]-4,5-dihydroimidazol-2-yl}nitramide) is a neonicotinoid which acts systemically on the central nervous system of insects. These active compounds work by causing a blockage in the nicotinergic neuronal pathway which leads to an accumulation of the neurotransmitter acetylcholine. This accumulation ultimately leads to the paralysis and death of the insect. Imidacloprid has chemical structure (I) below:

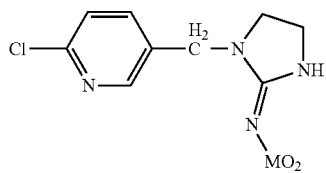

(I)

Suitable imidacloprid analogues have the chemical structure (II):

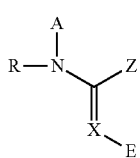

(II)

wherein

R is hydrogen or an optionally substituted radically selected from the group consisting of acyl, alkyl, aryl, aralkyl, heteroalkyl and heteroarylakyl;

A is a monofunctional group selected from the group consisting of hydrogen, acyl, alkyl, aryl, or a bifunctional group which is attached to the radical Z;

E is an electron withdrawing radical;

X is —CH= or =N—, wherein —CH= may be attached to the radical Z in place of the Hydrogen atom; and Z is a monofunctional group selected from the group consisting of alkyl, —O—R, —S—R, —N($R^1$)($R^2$), wherein $R^1$ and $R^2$ may be the same or different or Z is a bifunctional group which is attached to A or X; and $R^1$ and $R^2$ are independently selected from the group consisting of hydrogen, acyl, alkyl, aryl, aralkyl, heteroalkyl and heteroaralkyl.

The term "acyl" as used herein refers to a radical of formula —C—(O)—R', —S—(O)—R' or —P(O)R'$_2$. Examples of suitable acyl groups include alkyl carbonyl, arylcarbonyl, alkylsulfonyl, arylsulfonyl, (alkyl)(aryl)phosphoryl, all of which may be substituted.

The term "alkyl" is used herein to refer to monovalent, divalent or trivalent straight or branched, saturated, acyclic hydrocarbyl groups. Particular groups which may be mentioned include $C_{1-10}$ alkyl, in particular $C_{1-4}$ alkyl, specifically methyl, ethyl, isopropyl, sec- or tert-butyl, all of which may be substituted.

The term "aryl" is used herein to refer to monovalent, divalent or trivalent, aromatic, cyclic hydrocarbyl groups, such as phenyl or naphthyl (e.g. 1-naphthyl or 2-naphthyl), in particular phenyl.

The term "aralkyl" as used herein refer to an alkyl group in which one or more hydrogens has been replaced with an aryl group. Aralkyl which may be mentioned are phenylmethyl and phenethyl.

The term "heteroaryl" is used herein to refer to monovalent, divalent or trivalent, heteroaromatic, cyclic hydrocarbyl groups additionally containing one or more heteroatoms independently selected from O, S, N and $NR^T$, wherein $R^T$ is preferably H or $C_1$-$C_{10}$ alkyl. Particular mention is made of heteroaryl groups having up to 10 ring atoms and, as heteroatoms, N, O and S, in particular N. Specific mention may be made of thienyl, furyl, thiazolyl, imidazolyl, pyridyl, benzothiazolyl.

The term "heteroarylalkyl" is used herein to refer to heteroaryl groups substituted with one or more alkyl groups. Specific heteroarylalkyl groups which may be mentioned are heteroarylmethyl and heteroarylethyl having up to 6 ring atoms and, as heteroatoms, N, O, S, in particular N.

As indicated above, a number of the groups defined may optionally be substituted. Exemplary and preferred substituents include $C_{1-4}$ alkyl, in particular methyl, ethyl, n- and isopropyl and n-, iso- and tert-butyl; alkoxy having preferably 1 to 4, in particular 1 or 2, carbon atoms, such as methoxy, ethoxy, n- and isopropyloxy and n-, iso- and tert-butyloxy; alkylthio having preferably 1 to 4, in particular 1 or 2, carbon atoms, such as methylthio, ethylthio, n- and isopropylthio and n-, iso- and tert-butylthio; haloalkyl having preferably 1 to 4, in particular 1 or 2, carbon atoms and preferably 1 to 5, in particular 1 to 3, halogen atoms, where the halogen atoms are identical or different and are preferably fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino having preferably 1 to 4, in particular 1 or 2, carbon atoms per alkyl group, such as methylamino, methylethylamino, n- and isopropylamino and methyl-n-butylamino; carboxyl; carbalkoxy having preferably 2 to 4, in particular 2 or 3, carbon atoms, such as carbomethoxy and carboethoxy; sulpho (—SO3H); alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl, and also heteroarylamino and heteroarylalkylamino, such as chloropyridylamino and chloropyridylmethylamino.

Preferred examples of the substituents, A, Z, E and X are as follows.

A is preferably hydrogen and also represents optionally substituted radicals from the group consisting of acyl, alkyl, aryl, which are preferably as defined under R. A may alternatively be a bifunctional group. In this regard, examples include optionally substituted alkylene having 1-4, in particular 1-2, carbon atoms, substituents which may be mentioned being the substituents listed further above, where the alkylene groups may be interrupted by heteroatoms from the group consisting of N, O and S.

A and Z together with the atoms to which they are attached may form a saturated or unsaturated heterocyclic ring. The heterocyclic ring may contain a further 1 or 2 identical or different heteroatoms and/or hetero groups. Preferred heteroatoms are oxygen, sulphur or nitrogen and preferred hetero groups are N-alkyl, where the alkyl of the N-alkyl group contains preferably 1 to 4, in particular 1 or 2, carbon atoms. Alkyl which may be mentioned are methyl, ethyl, n- and isopropyl and n-, iso- and tert-butyl. The heterocyclic ring contains 5 to 7, preferably 5 or 6, ring members.

Examples of the heterocyclic ring include pyrrolidine, piperidine, piperazine, hexamethyleneimine, hexahydro-1,3,5-triazine, morpholine, which may optionally be substituted, preferably by methyl.

E may be an electron-withdrawing radical, where mention may be made in particular of $NO_2$, CN, haloalkylcarbonyl, such as 1,5-halo-$C_{1-4}$-carbonyl, in particular $COCF_3$.

X may be —CH= or —N=.

Z may be optionally substituted radicals alkyl, —OR, —SR, —NRR, where R and the substituents preferably have the meaning given above.

Z can furthermore, in addition to the ring mentioned above, form, together with the atom to which it is attached and the radical =C(CH$_3$)— instead of X, a saturated or unsaturated heterocyclic ring. The heterocyclic ring may contain a further 1 or 2 identical or different heteroatoms and/or hetero groups. Preferred heteroatoms are oxygen, sulphur or nitrogen and preferred hetero groups are N-alkyl, where the alkyl or N-alkyl group contains preferably 1 to 4, in particular 1 or 2, carbon atoms. Alkyl which may be mentioned are methyl, ethyl, n- and isopropyl and n-, iso- and tert-butyl. The heterocyclic ring contains 5 to 7, preferably 5 or 6, ring members.

Examples of the heterocyclic ring include pyrrolidine, piperidine, piperazine, hexamethyleneimine, morpholine and N-methyl-piperazine.

Preferred imidazole analogues for use in the composition of the present invention include the compounds of formula (III) and formula (IV) below:

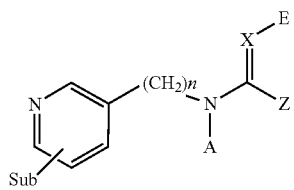
(III)

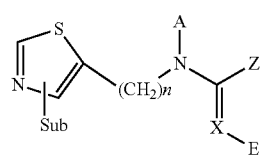
(IV)

Particularly suitable imidacloprid analogues include:

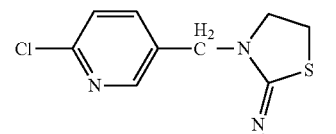
Thiacloprid

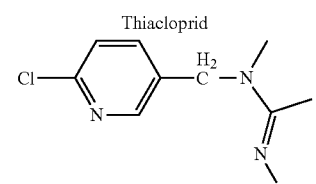
Acetamprid

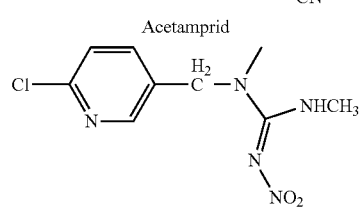
Ti 304

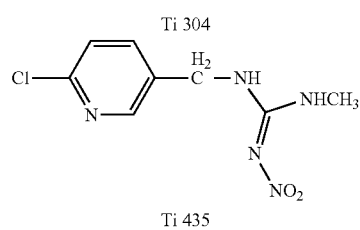
Ti 435

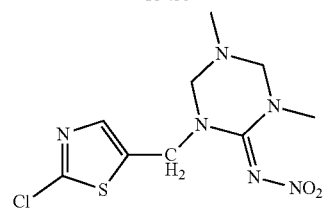
AKD 1022

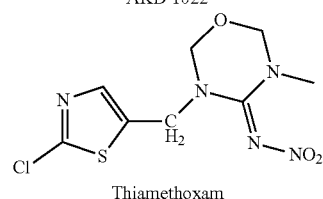
Thiamethoxam

The imidacloprid or analogue thereof is included in the compositions of the present invention in an amount in the range from about 0.1% to about 20% by weight, preferably in the range from about 1% to about 15% by weight, more preferably in the range from about 2.5% to about 12.5% by weight.

The compositions of the present invention further comprise a pyrethroid. A pyrethroid is an organic compound similar to the natural pyrethrins produced by the flowers of pyrethrums (*Chrysanthemum cinerariaefolium* and *C. coccineum*). Pyrethroids function as neurotoxins, affecting neural membranes by prolonging sodium channel activation. Examples of suitable pyrethoids include acrinathrin, allethrin, bifenthrin, bioallethrin, bioallethrin S-cyclo pentenyl isomer, bioresmethrin, cycloprothrin, cyfluthrin, beta-cyfluthrin, cyhalothrin, lambda cyhalothrin, cypermethrin, including the resolved isomers alpha-cypermethrin, beta-cypermethrin and zeta-cypermethrin, cyphenothrin, deltamethrin, empenthrin, esfenvalerate, etofenprox, fenpropathrin, fenvalerate, flucythrinate, tau-fluvalinate, flumethrin, imiprothrin, lambda-cyhalothrin, metofluthrin, permethrin, phenothrin [(1R)-trans-isomer], prallethrin, resmethrin, RU15125, silafluofen, sumithrin, tau-fluvalinate, tefluthrin, tetramethrin, tetramethrin [(1R)-isomers], tralomethrin, transfluthrin, transflumethrin. Different pyrethroids will be suitable depending on the animal which is to be treated with the veterinary composition of the present invention and the skilled person will be familiar with appropriate pyrethroids to select. For example, permethrin is known to be toxic for cats. Preferably, the pyrethroid is selected from the group consisting of etofenprox, deltamethrin, permethrin, cyfluthrin, flumethrin, cypermethrin, cyphenothrin, fenvalerate, esfenvalerate and lambda-cyhalothrin. In one embodiment, the pyrethroid is selected from the group consisting of etofenprox, deltamethrin, cyfluthrin, flumethrin, cypermethrin, cyphenothrin, fenvalerate, esfenvalerate and lambda-cyhalothrin.

The veterinary compositions of the present invention comprise the pyrethroid in an amount in the range from about 0.1% to about 75% by weight. The amount of pyrethroid which is present will depend on the pyrethroid. For example, where the pyrethroid is deltamethrin, it is preferably included in an amount in the range from about 0.1% to about 20% by weight. Alternatively, where the pyrethroid is etofenprox, it is preferably included in an amount in the range from about 0.1% to about 60% by weight. Alternatively, where the pyrethroid is permethrin, it is preferably included in an amount in the range from about 0.1% to about 70% by weight. Alternatively, where the pyrethroid is flumethrin, it is preferably included in an amount in the range from about 0.1% to about 25% by weight. Alternatively, where the pyrethroid is cyfluthrin, it is preferably included in the amount in the range from about 0.1% to about 25% by weight. Alternatively, where the pyrethroid is cypermethrin, it is preferably included in an amount in the range from about 0.1% to about 60% by weight. Alternatively, where the pyrethroid is cyphenothrin, it is preferably included in an amount in the range from about 0.1% to about 60% by weight. Alternatively, where the pyrethroid is fenvalerate, it is preferably included in an amount in the range from about 0.1% to about 60% by weight. Alternatively, where the pyrethroid is esfenvalerate, it is preferably included in an amount in the range from about 0.1% to about 60% by weight. Alternatively, where the pyrethroid is lambda-cyhalothrin, it is preferably included in an amount in the range from about 0.1% to about 25% by weight.

Preferably, the compositions of the present invention comprise permethrin. Permethrin ((3-phenoxyphenyl) methyl 3-(2,2-dichloroethenyl)-2,2-dimethylcyclopropanecarboxylate) is an insecticide which is known for the treatment of parasites on animals. An advantage of using permethrin as the pyrethroid in the veterinary compositions of the present invention is that it is known to possess a repellancy effect. This repellancy effect is useful in preventing flea allergy dermatitis (FAD), an immunological response to the flea saliva by preventing the fleas from actually biting the animal.

The compositions of the present invention preferably comprise permethrin in an amount in the range from about 25% to about 75% by weight, preferably about 35% to about 67.5% by weight, preferably in an amount in the range from about 40% to about 67.5% by weight, more preferably in an amount in the range from about 42.5% to about 67.5% by weight. Commercially available sources of permethrin may comprise an isomeric mixture of cis-permethrin and trans-permethrin with the typical cis:trans ratios available being 25:75, 40:60 and 80:20. It is within the knowledge of the skilled person to adjust the amount of permethrin included with the veterinary compositions of the present invention in order to account for the particular isomeric ratio of the source of permethrin used.

The compositions of the present invention may comprise one or more further active ingredients. In one embodiment, the compositions of the present invention may comprise pyriproxifen. Pyriproxifen (2-[1-(4-phenoxyphenoxy)propan-2-yloxy]pyridine, CAS No. 95737-68-1) is a juvenile hormone analogue. Where present, pyriproxyfen may be included in an amount of up to about 2% by weight.

Alternatively or in addition, in order to broaden the spectrum of activity, the compositions of the present invention may comprise up to about 40% by weight, alternatively up to about 30% by weight, alternatively up to about 20% by weight of one or more veterinary acceptable endoparasitic and exoparasitic agents. Examples of suitable agents include, but are not limited to, ivermectin, avermectin, milbemycin, methoprene, trifluron, fenoxycarb, lufenuron, cyromazine, diflubenzuron; amitraz, propoxur, cythioate, moxydectin, selamectin and isoxazolines. Where an endoparasitic agent is included within the compositions of the present invention, it will have a systemic effect while the activity of the combination of the imidacloprid and the pyrethroid remains non-systemic.

In addition to the active ingredients, imidacloprid or an analogue thereof and permethrin, the balance of the compositions of the present invention by weight comprises a first solvent selected from the group consisting of NMP and N-ethylpyrrolidone (NEP) and mixtures thereof and a second solvent which is DMSO. As described above, with regard to safety, NMP has been classified as a category 2 solvent which means that great care needs to be taken when it is handled. In contrast, DMSO is classified as a class 3 solvent by the FDA. Thus, by including DMSO as an essential component, the amount of NMP or NEP which is required has been reduced and so the compositions of the present invention can be manufactured more safely than currently available formulations which comprise the same active ingredients.

The present inventor has also surprisingly found that where the compositions include this combination of solvents then the compositions can be stored at low temperatures (i.e. about 5° C.) without any crystallisation being observed. This is not the case with the currently available commercial products.

The avoidance of crystallisation is important in order to ensure that the compositions perform in the way in which is intended after application to the animal. More specifically, as has been described previously, while the compositions are not systemically active on the animal to which they are applied, it is important that the formulations remain in a liquid form for a period which is sufficiently long that they can penetrate through to the lower dermal layers (i.e. stratum corneum) and hence then spread over the body of the animal. In addition to penetrating to the lower dermal layers, it is believed that spreading of the active ingredients included within the formulations from a single application locus also occurs as a consequence of dissolution in the animal's sebum. Without wishing to be bound by theory, it is also believed that, as a consequence of dissolution in the sebum, a reservoir of active ingredients is formed within the sebaceous glands which may account for the long term duration of the compositions of the present invention. These effects cannot occur where the active ingredients crystallise out of solution.

Furthermore, during transport of the compositions prior to sale through various climate zones, it is likely that low temperatures will be encountered. In such a situation, if the compositions are prone to crystallisation then lower efficacy will be observed when they are ultimately used on an animal.

The terms "systemically active" and "systemic effect" are used herein to refer to an effect or efficacy only when intracorporeally present within the target pest, such as after ingestion or other administration which results in the presence of both active agents in the target pest. Other than when used in respect of an optionally present endoparasitic agent, the term does not mean having a deleterious effect when present within the system of a host domestic animal, it is limited to activity or efficacy when intracorporeally present within a pest.

As described above, it is essential that the compositions include at least some DMSO. Without wishing to be bound by theory, it is believed that the presence of the DMSO prevents the composition from crystallising at low temperature and only small amounts of DMSO are required in order to observe this change. In this regard, the compositions of the present invention may comprise at least about 2.5% by weight of DMSO, alternatively at least about 5% by weight, alternatively at least about 7.5% by weight, alternatively at least about 10% by weight of DMSO. From the viewpoint of improving safety, it is advantageous to replace as much NMP as possible, while still providing a composition which is effective. In this regard, the compositions of the present invention may include greater than 10% by weight, alternatively greater than 12% by weight of DMSO. The content of DMSO is preferably less than about 97.3% by weight, preferably less than about 80% by weight, preferably less than about 60%, preferably less than about 50%, in some embodiments, less than about 45% by weight. Thus, in one embodiment, the content of DMSO may be in the range from about 2.5% to about 60% by weight, in one embodiment, it may be in the range from about 7.5% to about 40% by weight, alternatively in the range from about 10% to about 30% by weight, alternatively in the range from about 15% to about 27.5% by weight, in one embodiment, in the range from about 17.5% to about 27.5% by weight. In some embodiments, the compositions of the present invention include at least 2.5% but less than 20% by weight of DMSO. For example, a composition of the invention may include between (a) 2.5% and 5%, (b) 2.5% and 10%, (c) 2.5% and 15%, (d) 2.5% and 20%, (e) 5% and 10%, (f) 5% and 15%, (g) 5% and 17%, (h) 5% and 18%, (i) 5% and 19%, (j) 5% and 20%, (k) 10% and 15%, (l) 10% and 17%, (m) 10% and 18%, (n) 10% and 19%, (o) 10% and 20%, (p) 15% and 17%, (q) 15% and 18%, (r) 15% and 19%, (s) 15% and 20%, (t) 17% and 18%, (u) 17% and 19%, (v) 17% and 20%, (w) 18% and 19%, (x) 18% and 20%, or (y) 19% and 20% by weight of DMSO. In certain embodiments, a composition of the present invention includes 15 to 19% by weight of DMSO. In particular embodiments, a composition of the present invention includes between 17% and 19% by weight of DMSO.

However, while including DMSO improves the safety of the compositions of the present invention, the inventor has surprisingly found that it is still not possible to completely eliminate the use of NMP, NEP or a mixture thereof. In this regard, while literature may suggest that DMSO may simply be substituted for NMP, the inventor has found that if DMSO is used alone in the present compositions then the crystallisation properties of the compositions are not suitable. More specifically, it has been found that the active ingredients crystallise out of the solution too quickly (i.e. before penetration to the lower dermal layers has been achieved) and so the resulting compositions suffer from lower efficacy.

Therefore, the compositions of the present invention may comprise the first solvent in an amount of at least about 2.5% by weight, alternatively at least about 5% by weight, alternatively at least about 7.5% by weight. From the viewpoint of improving safety, it is advantageous to minimise the content of the first solvent to the extent that this is possible while still maintaining efficacy. In this regard, the compositions of the present invention may include less than about 27.5% by weight, preferably less than about 25% by weight of the first solvent. Thus, the content of the first solvent may be in the range from about 2.5% to about 25% by weight. In some embodiments, the compositions of the present invention include greater than 20% by weight of the first solvent. For example, a composition of the present invention may include from (a) greater than 20% and up to 27.5%, (b) 21 to 27.5%, (c) 22 to 27.5%, (d) greater than 20% and up to 25%, (e) 21 to 25%, (f) 22 to 25%, (g) greater than 20% and up to 23%, (h) 21 to 23%, or (i) 22 to 23% by weight of the first solvent. In particular embodiments, a composition of the present invention includes between 21 and 23% by weight of the first solvent. In particular embodiments, the first solvent is N-methyl pyrrolidone.

The compositions of the present invention may further comprise up to 5% by weight of water (e.g., 0%, 1%, 2%, 3%, 4%, or 5% by weight).

In addition to the components already discussed, the compositions of the present invention may further comprise an anti-oxidant. An anti-oxidant is included for the purpose of preventing degradation and thus improving the stability of the compositions. Where included, an anti-oxidant may be present in an amount of up to about 0.5% by weight (e.g., 0%, 0.05%, 0.1%, 0.15%, 0.2%, 0.25%, 0.3%, 0.35%, 0.4%, 0.45%, or 0.5% by weight). Where present, an anti-oxidant is preferably included in an amount in the range from about 0.05% to about 0.25% by weight. The skilled person will be familiar with suitable anti-oxidants for incorporation into veterinary compositions. Examples include phenolic anti-oxidants which as butylated hydroxytoluene, butylated hydroxyanisole and tocopherol.

Alternatively or in addition, the compositions of the present invention may further comprise up to about 2% by weight of an organic acid (e.g., 0%, 0.5%, 1%, 1.5%, or 2% by weight). Preferably, where present, an organic acid may be included in an amount in the range from about 0.05% to about 1% by weight. Suitable organic acids include all organic acids which are acceptable for use in veterinary and pharmaceutical products. Examples include carboxylic acids such as citric acid, tartaric acid, lactic acid, succinic acid and malic acid. Citric acid is preferred.

The compositions of the present invention may also further comprise, typically in an amount of up to about 40% by weight (e.g., 0%, 5%, 10%, 15%, 20%, 25%, 30%, 35%, or 40% by weight), of one or more further veterinary acceptable excipients. Examples of such excipients include but are not limited to surfactants and spreading agents. Suitable surfactants include non-ionic surfactants, such as polyethoxylated castor oil, polysorbates (ethoxylated esters or partial esters of sorbitol), polyethoxylated sorbitan monooleate, sorbitan monostearate, glycerol monostearate, polyoxystearate, alkylphenol polyglycol ethers, polyoxyethylene alkyl ethers and esters, polyoxyethylene alkylphenols and poloxamers (polyoxyethylene-polyoxypropylene block copolymers); ampholytic surfactants such as di-sodium N-lauryl-β-imino-dipropionate or lecithin, phosphatidylcholine, alkyl betaines (e.g. cocamidopropyl betaine); anionic surfactants, such as sodium lauryl sulphate, fatty alcohol ether sulphates, mono/dialkyl polyglycol ether orthophosphoric acid ester monoethanolamine salt, sodium stearate; and cationic surfactants such as cetyltrimethylammonium chloride, cetyltrimethylammounium bromide, octadecylamine hydrochloride. Suitable spreading agents include spreading oils such as di-2-ethylhexyl adipate, isopropyl myristate, dipropylene glycol pelargonate, cyclic and acylic silicone oils, such as dimethicone and further co- and terpolymers thereof with ethylene oxide, propylene oxide and formaldehyde, fatty acid esters, triglycerides, fatty alcohols.

The compositions of the present invention are liquid and hence suitable for dermal application. Preferably the compositions of the present invention are pour-on or spot-on formulations.

The compositions of the present invention are useful for controlling a parasite on or within an animal. Accordingly, the present invention further provides a veterinary composition as defined herein, for use in controlling a parasite on or within a warm-blooded domesticated animal. The parasites are selected from the group consisting of ectoparasites, endoparasites or both.

The animal may be a small domesticated animal such as a cat, dog, rabbit, ferret or other warm-blooded animal. The compositions of the present invention are particularly useful for controlling a parasite on or within a dog, particularly where the pyrethroid is permethrin.

The parasite infecting the animal to be treated may be selected from one or more of the groups consisting of fleas, ticks, mites, lice, intestinal worms, heartworms and other internal worms and mixtures thereof. Examples of particular parasites which may be mentioned include parasites from the order of the Anoplura e.g. *Haematopinus* spp., *Linognathus* spp., *Solenopotes* spp., *Pediculus* spp., *Pthirus* spp.; from the order of the Mallophaga e.g. *Trimenopon* spp., *Menopon* spp., *Eomenacanthus* spp., *Menacanthus* spp., *Trichodectes* spp., *Felicola* spp., *Damalinea* spp., *Bovicola* spp.; from the order of the Diptera e.g. *Aedes* spp., *Culex* spp., *Simulium* spp., *Phlebotomus* spp., *Chrysops* spp., *Tabanus* spp., *Musca* spp., *Hydrotaea* spp., *Muscina* spp., *Haematobosca* spp., *Haematobia* spp., *Stomoxys* spp., *Fannia* spp., *Glossina* spp., *Lucilia* spp., *Calliphora* spp., *Auchmero-myia* spp., *Cordylobia* spp., *Cochliomyia* spp., *Chrysomyia* spp., *Sarcophaga* spp., *Wohlfartia* spp., *Gasterophilus* spp., *Oesteromyia* spp., *Oedemagena* spp., *Hypoderma* spp., *Oestrus* spp., *Rhinoestrus* spp., *Melophagus* spp., *Hippobosca* spp.; from the order of the Siphonaptera e.g. *Ctenocephalides* spp., *Echidnophaga* spp., *Ceratophyllus* spp., *Pulex* spp.; *Hystrichopsyllidae* spp., *Ctenopsyllidae* spp., *Amphipsyllidae* spp., from the order of the Metastigmata e.g. *Hyalomma* spp., *Rhipicephalus* spp., *Boophilus* spp., *Amblyomma* spp., *Haemaphysalis* spp., *Dermacentor* spp., *Ixodes* spp., *Argas* spp., *Ornithodorus* spp., *Otobius* spp.; from the order of the Mesostigmata e.g. *Dermanyssus* spp., *Ornithonyssus* spp., *Pneumonyssus* spp.; from the order of the Prostigmata e.g. *Cheyletiella* spp., *Psorergates* spp., *Myobia* spp., *Demodex* spp., *Neotrombicula* spp.; from the order of the Astigmata e.g. *Acarus* spp., *Myocoptes* spp., *Psoroptes* spp., *Chorioptes* spp., *Otodectes* spp., *Sarcoptes* spp., *Notoedres* spp., *Knemidocoptes* spp., *Neoknemidocoptes* spp. *Cytodites* spp., *Laminosioptes* spp., from the order Ascaridida, e.g. *Toxocaridae*, from the order Trichocephalida, e.g. *Trichuridae*, from the order Strongylida, e.g. *Ancylostomatidae*, *Filaroididae*, *Metastrongylidae* from the order Rhabditia, e.g. *Rhabditida* spp., from the order Cyclophyllidea, e.g. *Taeniidea, Mesocestoides* spp., *Dipylidiidae*, from the order Spirurida, e.g. *Onchocercidae*, *Thelaziidae*, from the order Trichurida, e.g. *Capillariidae*, *Crenosomatidae*.

When administered as a spot-on formulation, the compositions of the present invention are typically administered in an amount of approximately about 0.075 to about 0.25 ml per kg body weight of the animal to a single locus, typically between the shoulder blades of the animal. The characteristics of the compositions mean that they spread from the single locus across the skin of the animal. As described above, without wishing to be bound by theory, this is believed to be as a consequence of a combination of penetration to the lower dermal levels and spreading through sebum.

The compositions of the present invention are particularly effective in controlling both fleas and ticks. The term "controlling" as used herein means eradicating or substantially reducing an existing infestation, preventing a new infestation and preventing reinfestation from ectoparasites in the environment, including by the eradication or substantial reduction of ectoparasites in areas habitually visited by the animal, such as its resting place. In particular, in addition to providing long term stability under low temperature storage conditions i.e. in all climate zones, the compositions of the present invention are toxicologically acceptable, dermally-friendly and provide good long-term action of at least three to four weeks following administration of a small volume to the skin of the animal to be treated (for example 0.1 ml/kg body weight of the animal to be treated). Thus, the compositions of the present invention are at least as effective as the currently available products in treating fleas and ticks but offer improved safety and storage stability.

The compositions of the present invention show no crystallisation when stored at a temperature of about 5° C. for a period of 20 days or greater, preferably 30 days or greater, preferably 40 days or greater, preferably 50 days or greater.

The invention will now be illustrated further by reference to the following examples which are in no way intended to be limiting on the scope of the invention.

EXAMPLES

Solubility studies were performed in order to identify suitable alternative solvents for NMP in the formulation of a veterinary composition comprising imidacloprid and permethrin. The commercially available Advantix® (from Bayer) was used as a reference against which the compositions were tested.

The active ingredients used were Imidacloprid (CAS 128261-41-3) and Permethrin (CAS 52645-53-1).

The solvents tested were as follows:
N-methyl pyrrolidone (CAS 872-50-4)
N-ethyl pyrrolidone (CAS 2687-91-4)
Transcutol (CAS 111-90-0)
Dowanol dmp (CAS 34590-94-8)
Glycofurol (CAS 31692-85-0)
Polyvinylpyrrolidone (CAS 9003-39-8)
Propylene carbonate (CAS 108-32-7)
Dimethyl sulfoxide (CAS 67-68-5)
G-butyrolactone (CAS 96-48-0)
n-butanol (CAS 71-36-3)
RhodiaSolv IRIS (CAS 14035-94-0)
Armid® FMPC Details of the formulations tested are set out in Table 1 below.

Formulations 1 to 2A and A to I were formulated in 100 ml beakers to a total volume of 70 ml and the solubility of the active ingredients in the different solvents was assessed. 7.14 g of imidacloprid was added to the solvent mixture followed by 35.79 g of permethrin, warmed to a temperature of approximately 45° C. so that it is a clear liquid. The mixture was vigorously stirred throughout the additions. The formulations were then mixed for a further three hours at room temperature and the degree of dissolution was assessed.

Where dissolution was successful, the formulation was transferred into three pre-labelled 20 ml vials (to a fill of greater than 75%) which were tightly capped with a PE-lined cap. The three vials were then stored at 5° C., room temperature and 30° C., respectively and the samples were monitored for crystallisation. Residual formulation was transferred to a fourth pre-labelled 20 ml vial and kept at room temperature. The results obtained are presented in Table 1 below.

TABLE 1

| Formulations | 1 | 2 | 3 | 4 | 1A | 2A | Advantix Reference | A | B | C | D | E | F | G | H | I |
|---|---|---|---|---|---|---|---|---|---|---|---|---|---|---|---|---|
| mg/ml | | | | | | | | | | | | | | | | |
| imidacloprid | 100 | 100 | 100 | 100 | 100 | 100 | 100 | 100 | 100 | 100 | 100 | 100 | 100 | 100 | 100 | 100 |
| Permethrin | 500 | 500 | 500 | 500 | 500 | 500 | 500 | 500 | 500 | 500 | 500 | 500 | 500 | 500 | 500 | 500 |
| N-MP | 220 | 220 | 220 | 220 | 220 | 220 | 479 | 250 | 0 | 250 | 250 | 250 | 250 | 250 | 250 | 0 |
| Co-solvent | | | | | | | | | | | | | | | | |
| Transcutol | QS | | | QS | | | | | | | | | | | | |
| Dowanol dpm | | QS | | | | QS | | | | | | | | | | |
| Glycofurol | | | QS | QS | | | | | | | | | | | | |
| PVP | | | | 50 | | | | | | | | | | | | |
| Propylene Carbonate | | | | | 150 | 150 | | | | | | | | | | |
| DMSO | | | | | | | | 244 | 244 | | 110 | | 140 | | | |
| N-Ethylpyrrolidone | | | | | | | | | 250 | | | | | | | |
| G-Butyrolactone | | | | | | | | | | | | | | 249 | | |
| n-Butanol | | | | | | | | | | 180 | 100 | | | | | |
| Rhodiasolv IRIS | | | | | | | | | | | | 235 | 100 | | | |
| Armid FMPC | | | | | | | | | | | | | | | 258 | QS |

Results of formulation-including temperature testing at 30 C., Room Temp and 5 C.
Formulations 1 and 2 could not dissolve all of the active ingredients, imidacloprid and permethrin
Formulation 3 formed cloudy phase separation, wherein addition of PVP (Formulation 4) only delayed cloudy precipitation formation
Formulations 1A and 2A (adding Propylene Carbonate) formed cloudy precipitation
Formulations C and E could not dissolve all of the active ingredients but Formulation F did work (due to addition of DMSO)
Formulations A and B worked well-went on to show best low temp 5 C. stability of any product (including Advantix)
Formulation D initially good but developed precipitate at 5 C. within 24 hours
Formulation G developed crystals within 24 hrs at 5 C., these continued to grow
Both Formulations H and I developed crystal formation and growth
Advantix developed crystals on day 16 at 5 C.
Formulations A and B did not develop crystals at any time point during 56 days testing at 5 C., room temp or 30 C.

Results

As set out in Table 1, in Formulations 1, 2, 3, 4, 1A, 2A, C and E, the active ingredients did not dissolve properly and so these formulations were rejected, with no further analysis based on these being carried out. In the remaining formulations, the active ingredients were dissolved and so storage tests at 5° C., room temperature and 30° C. were performed.

While formulation D looked promising initially, a precipitate was formed after only 24 hours storage at 5° C. indicating that such a composition would not be suitable due to storage problems. A similar problem was observed with formulations F, G, H and I.

Interestingly, the Advantix® formulation which was used as a reference for these experiments was observed to form crystals after storage at 5° C. for 16 days indicating that this formulation suffers from long term stability problems following storage at low temperatures.

Formulations A and B showed excellent results and did not demonstrate any crystal growth after storage for 56 days at 5° C., room temperature and 30° C. Formulation comprises a mixture of NMP and DMSO, while formulation B comprises a mixture of NEP and DMSO.

What is claimed is:

1. A method of controlling parasites on a warm-blooded animal comprising:
    applying to skin of an animal to be treated, a veterinary composition comprising:
    2.5% to 12.5% by weight of imidacloprid or an analogue thereof;
    35% to 67.5% by weight of permethrin;
    0.1% to 2% by weight of pyriproxyfen;
    a first solvent of 21% to 23% by weight, selected from the group consisting of N-methyl pyrrolidone, N-ethyl pyrrolidone and mixtures thereof; and
    a second solvent of 15% to less than 20% by weight of dimethyl sulfoxide (DMSO).

2. The method according to claim 1, wherein the parasites are selected from the group consisting of ectoparasites, endoparasites or both.

3. The method according to claim 1, wherein the parasites are selected from one or more of the groups consisting of fleas, ticks, mites, lice, intestinal worms, and heartworms.

4. The method according to claim 1, wherein the animal is a dog.

5. The method according to claim 1, wherein the second solvent of the veterinary composition is 17% to 19% by weight of DMSO.

6. The method according to claim 1, wherein the first solvent of the veterinary composition is N-methyl pyrrolidone.

7. The method according to claim 1, wherein the first solvent of the veterinary composition is N-ethyl pyrrolidone.

8. The method according to claim 1, wherein the veterinary composition further comprises an antioxidant in an amount in the range from about 0.05% to about 0.25% by weight.

9. The method according to claim 1, wherein the veterinary composition further comprises at least one organic acid in an amount in the range from about 0.05% to about 1% by weight.

* * * * *